United States Patent [19]

Ward, III et al.

[11] Patent Number: 4,554,370

[45] Date of Patent: Nov. 19, 1985

[54] METHOD FOR MAKING ALKYLHALOSILANES

[75] Inventors: William J. Ward, III, Schenectady; Alan Ritzer, Sand Lake; Heine Lapidot, Latham, all of N.Y.

[73] Assignee: General Electric Company, Schenectady, N.Y.

[21] Appl. No.: 665,878

[22] Filed: Oct. 29, 1984

[51] Int. Cl.$^4$ ............................................... C07F 7/16
[52] U.S. Cl. .................................................. 556/472
[58] Field of Search ....................................... 556/472

[56] References Cited

U.S. PATENT DOCUMENTS 3,133,109   5/1964   Dotson ................................. 556/472
4,487,950  12/1984   Ward et al. .......................... 556/472

FOREIGN PATENT DOCUMENTS 130882   3/1960   U.S.S.R. .............................. 556/472
400594   3/1974   U.S.S.R. .............................. 556/472

OTHER PUBLICATIONS

Cab-O-Sil in Coatings, Product Data Sheet from the Cabot Corporation, published prior to 10/29/84.

Primary Examiner—Paul F. Shaver
Attorney, Agent, or Firm—William A. Teoli; James C. Davis, Jr.; James Magee, Jr.

[57] ABSTRACT

The use of fumed silica in a mixture of powdered silicon and cuprous chloride has been found to reduce agglomeration in a fluid bed reactor during the production of alkylhalosilane under continuous conditions.

3 Claims, No Drawings

METHOD FOR MAKING ALKYLHALOSILANES

BACKGROUND OF THE INVENTION

The present invention relates to a method for making alkylhalosilanes. More particularly, the present invention relates to a process involving the reaction of methyl chloride and powdered silicon in the presence of a copper chloride catalyst and a minor amount of fumed silica.

As taught by Rochow, Chemistry of the Silicones, Second Edition, John Wiley & Sons (1951), Cuprous Chloride, can be deposited on the grains of silicon by reduction to provide a reactive contact mass for the synthesis of chlorosilanes from methyl chloride and powdered silicon. Those skilled in the art know that cuprous chloride has a tendency to sinter when heated to temperatures exceeding 230° C., which interferes with its use as an attractive copper source for the direct method of making methylchlorosilanes in a fluid bed reactor. It has been known, for example, that "clumping" or caking of the mixture of cuprous chloride and powdered silicon can occur in the fluid bed which can interfere with the performance of the resulting copper-silicon contact mass in converting methyl chloride and powdered silicon to methylchlorosilanes. Agglomeration of the cuprous chloride powdered silicon contact mass can be alleviated to some extent by mechanical agitation, such as provided by a stirrer. However, agglomeration of the cuprous chloride-powdered silicon mixture prior to the formation of copper-silicon contact mass in the fluid bed can seriously interfere with fluid bed performance. It would be desirable to be able to use cuprous chloride as a source of copper in a fluid bed reactor as other forms of copper compounds, such as copper oxide, can be used.

The present invention is based on the discovery that a mixture comprising powdered silicon, fumed silica and cuprous chloride fed intermitently or on a continuous basis to a fluid bed reactor can result in no caking. Evidence of clumping in a fluid bed reactor when it is running under continuous conditions can be shown by irregular hot spots as detected with thermocouples.

STATEMENT OF THE INVENTION

There is provided by the present invention, a method for making alkylhalosilanes in a fluid bed reactor which comprises, effecting contact between alkylhalide and a copper-silicon contact mass which is generated in situ in the reactor by introducing into the fluid bed reactor, under continuous conditions, a mixture comprising 100 parts of powdered silicon, 0.001 to 0.2 part of fumed silica, and 0.1 to 20 parts of cuprous chloride.

It is particularly preferred to practice the method of the present invention in a fluid bed reactor in a continuous manner, where silicon material having catalyst values is elutriated from the reactor and recycled.

Although methyl chloride is preferably used in the practice of the present invention, other $C_{(1-4)}$ alkylchlorides, for example, ethyl chloride, propyl chloride, etc., also can be used.

Methyl chloride, or an inert gas such as argon, or mixture thereof, can be used to fluidize the bed of silicon particles in the reactor with or without catalyst values. The silicon present in the fluidized bed can have a particle size below 700 microns, with an average size of greater than 20 microns and less than 300 microns in size. The mean diameter of the silicon particles is preferably in the range of 100 to 150 microns.

Silicon is usually obtained at a purity of at least 98% by weight of silicon and it is then comminuted to particles of silicon in the above-described range, and is fed into an appropriate reactor as needed. Although a fluidized bed is preferred, the process of the present invention can be utilized in other types of reactors, such as fixed bed and a stirred bed. A fluidized reactor is preferably utilized since the optimum selectivity and the maximum amount of methylchlorosilane is obtained. The process of the present invention can be carried out at a temperature in the range of 250–350° C. and more preferably at a temperature range of 270°–330° C. Reaction can occur under continuous conditions or as a batch reaction.

It is also advisable to carry out the process of the present invention under a pressure of 1–10 atmospheres.

Methyl chloride gas can be continuously passed through the reactor to fluidize the reaction mass and there can be passed out of the reactor, gaseous methylchlorosilanes as well as the unreacted methyl chloride. The gaseous crude product mixture and entrained reaction particulates are passed out of the fluidized reactor and passed through one or more cyclones so as to separate the larger particles of materials from the product gas stream. These particles can be returned to the reactor for further utilization in the process so as to maximize the yield of dimethyldichlorosilane from the silicon. Smaller particles are passed out with the product stream and the stream is subsequently condensed.

Purified methyl chloride is heated and recycled through the fluidized reactor for the further production of methylchlorosilanes. The crude methylchlorosilane stream is passed to a distillation train so as to distill out in essentially pure form various chlorosilane fractions produced by the process. It is necessary to distill and purify the dimethyldichlorosilane and the other chlorosilanes so that they can be utilized in the process for producing silicone materials.

The methyl chloride which is passed or subjected to the direct process in the fluidized bed reactor is heated to the temperature above its boiling point and passed as a gas at sufficient rate through the reactor to fluidize the bed of silicon particles.

The process of the present invention can be carried out in a fluid bed reactor having a jet mill at the bottom. A suitable jet mill arrangement is shown by Dotson, U.S. Pat. No. 3,133,109, wherein large silicon particles are comminuted. The resulting finer particles of silicon and catalyst can be further used in the reactor to produce the desired alkylhalosilane.

Another method of improving silicon utilization involves abrading the surface of silicon particles. Treatment of small and large silicon particles is shown by Shade U.S. Pat. No. 4,281,149 which is assigned to the same assignee as the present invention and hereby incorporated by reference. Shade advantageously effects the removal of smaller silicon particles from the fluidized bed reactor, abrades and thereafter recycles the particles.

The term cuprous chloride as used hereinafter means a material having a particle size of less than 325 ASTM mesh. The term fumed silica means a product produced by hydrolyzing silicon tetrachloride, or other chlorosilicon compound, such as trichlorosilane vapor in a flame of hydrogen and oxygen. It can have a surface area of 200 to 420 square meters per gram. Included by the term fumed silica are Cab-O-Sil manufactured by Cabot Corporation and DeGussa Aerosil.

In order that those skilled in the art will be better able to practice the invention, the following examples are given by way of illustration and not by way of limitation. All parts are by weight.

EXAMPLE.

The direct synthesis of methylchlorosilanes via granular silicon and methyl chloride is continuously conducted in a fluid bed reactor with mixed copper oxide catalyst; the copper source is abruptly changed to cuprous chloride, having a $-325$ ASTM mesh particle size. There is fed into the reactor on a continuous basis over a period of 70 hours, a mixture of 100 parts of silicon, 10 parts of cuprous chloride and about 0.1 part of fumed silica (De Gussa Aerosil 200). There is no evidence of agglomeration or fluid bed caking as shown by lack of drift of temperature points from "multi-pack" reactor thermocouples, and no increase in diffusor plate $\Delta P$, or "stones or agglomerates" beyond those normally observed upon reaction termination.

A similar run is conducted in a fluidized-bed reactor involving direct reaction between granular chemical grade silicon (98.5% Si) and methyl chloride at 280°–300° C. in which the catalyst source is a naturally-occurring precipitate based mixed copper oxide, which also is abruptly changed to a powdered cuprous chloride. The cuprous chloride contains 99% copper as $Cu_2Cl_2$ and the particle size is $-100$ ASTM mesh. The cuprous chloride is pre-blended with 5 weight percent of the aforementioned copper oxide powder to enhance flowability to enable use of a mechanical-pneumatic feed system. However, fumed silica is not premixed with the cuprous chloride before it is fed into the reactor.

After a feed period of 72 hours it is found that fluid bed caking or agglomeration of contact mass occurs. Agglomeration is based on the spreading of multipoint temperature measurements (via thermocouples) increased $\Delta P$ across diffusor plate, and evidence of solid cake upon transferring "spent bed" at termination of the reactor run.

These results show that powdered cuprous chloride can be used as a source of copper catalyst in a fluid bed reactor under continuous conditions without agglomeration occuring if the cuprous chloride is fed into the reactor along with fumed silica in accordance with the practice of the invention.

Although the above examples are directed to only a few of the very many variables which can be used in the practice of the method of the present invention, it should be understood that the present invention is directed to the use of a much broader variety of cuprous chloride material such as the use of a mixture of cuprous chloride in combination with other amounts of powdered silicon, and fumed silica along with other metals or metal compounds used as promoters or cocatalysts.

What we claim as new and desire to secure by Letters Patent of the United States is:

1. A method for making alkylhalosilanes in a fluid bed reactor which comprises, effecting contact between alkylhalide and powdered silicon in the presence of a copper-silicon contact mass which is generated in situ in the reactor by introducing into the fluid bed reactor, under continuous conditions, a mixture comprising 100 parts of powdered silicon, 0.001 to 0.2 part of fumed silica, and 0.1 to 20 parts of cuprous chloride.

2. A method in accordance with claim 1, where the alkylhalide is methyl chloride.

3. A method for making methylchlorosialnes which comprises effecting contact between methyl chloride and powdered silicon in the presence of a copper-silicon contact mass which is generated in situ in a stirred bed reactor by introducing into the stirred bed reactor a mixture comprising 100 parts of powdered silicon, 0.001 to 0.2 part of fumed silica, and 0.1 to 20 parts of cuprous chloride.

* * * * *